US007291012B2

United States Patent
Lyren

(10) Patent No.: US 7,291,012 B2
(45) Date of Patent: Nov. 6, 2007

(54) DENTAL IMPLANT WITH POROUS BODY

(76) Inventor: Philip S. Lyren, 2515 Willowby Dr., Houston, TX (US) 77008

( * ) Notice: Subject to any disclaimer, the term of this patent is extended or adjusted under 35 U.S.C. 154(b) by 662 days.

(21) Appl. No.: 10/375,343

(22) Filed: Feb. 27, 2003

(65) Prior Publication Data

US 2004/0170946 A1    Sep. 2, 2004

(51) Int. Cl.
A61C 8/00      (2006.01)
(52) U.S. Cl. .................................... 433/173
(58) Field of Classification Search ............. 433/173, 433/174, 175, 176
See application file for complete search history.

(56) References Cited

U.S. PATENT DOCUMENTS

| | | | |
|---|---|---|---|
| 3,797,113 A * | 3/1974 | Brainin | 433/173 |
| 3,934,347 A * | 1/1976 | Lash et al. | 433/173 |
| 4,186,486 A * | 2/1980 | Gordon | 433/201.1 |
| 4,244,689 A * | 1/1981 | Ashman | 433/175 |
| 4,379,694 A * | 4/1983 | Riess | 433/201.1 |
| 4,439,152 A * | 3/1984 | Small | 433/173 |
| 4,447,209 A * | 5/1984 | Sutter | 433/173 |
| 4,842,517 A * | 6/1989 | Kawahara et al. | 433/173 |
| 4,957,819 A * | 9/1990 | Kawahara et al. | 428/547 |
| 5,002,488 A * | 3/1991 | Homsy | 433/169 |
| 5,049,074 A * | 9/1991 | Otani et al. | 433/173 |
| 5,383,935 A * | 1/1995 | Shirkhanzadeh | 623/23.49 |
| 5,914,185 A | 6/1999 | Shoher et al. | |
| 5,989,027 A | 11/1999 | Wagner et al. | |
| 6,302,913 B1 | 10/2001 | Ripamonti et al. | |
| 6,379,153 B1 * | 4/2002 | Schroering | 433/173 |

FOREIGN PATENT DOCUMENTS

WO      WO 02/34155      * 5/2002

* cited by examiner

Primary Examiner—Ralph A. Lewis

(57) ABSTRACT

A dental implant having two distinct regions, a coronal region and a bone fixation region. The coronal region has a smooth transgingival section and an interface for connecting to a dental component. The bone fixation region has an elongated cylindrical shape and is formed as a porous structure that extends completely through the bone fixation region.

1 Claim, 2 Drawing Sheets

DENTAL IMPLANT WITH POROUS BODY

FIELD OF THE INVENTION

The disclosure herein generally relates to dental implants for osseointegration in alveolar bone and, more particularly, to dental implants having a porous body.

BACKGROUND OF THE INVENTION

Much effort has been directed to integrating dental implants into surrounding bone. Ideally, a dental implant would be placed into alveolar bone, and thereafter bone would readily grow into the surface of the implant. To achieve this objective, many different surface technologies have been applied to dental implants. In some instances, the surface of the implant is roughened, grit-blasted, plasma-sprayed, or microtextured. In other instances, the surface is coated with a biological agent, such as hydroxylapatite (known as HA). In all of these instances, the goal is the same: Produce a surface on the dental implant into which surrounding bone will grow or bond.

Porous coatings have also been applied to surfaces of dental implants. U.S. Pat. No. 5,989,027 entitled: "Dental Implant Having Multiple Textured Surfaces" to Wagner et al. (and expressly incorporated herein by reference) teaches a dental implant having multiple textured surfaces on the same implant. One surface includes a porous coated substrate, and another surface includes a nonporous surface adapted to encourage bone growth or bonding.

Porous coatings are advantageous since bone will indeed grow into the surface of the implant. Osseointegration, to a limited extent then, has been achieved with porous coated surfaces. These surfaces though are far from ideal in terms of accepting and encouraging bone growth into the body of the implant.

As one disadvantage, porous surfaces are often thin coatings applied to the metallic substrate of the implant. Bone surrounding the implant can only grow into the coating itself. Bone cannot grow through the coating and into the metallic substrate. The depth of bone growth into the implant is limited to the depth of the porous coating. Bone simply cannot grow completely through the implant.

As another disadvantage, porous surfaces on dental implants do not have the proper geometric size and structure to maximize bone growth into the implant. A porous structure that more closely emulated the size and structure of bone itself would more fully accept and encourage bone growth and bonding into the structure.

It therefore would be desirable to have a dental implant that offers optimum anchoring in bone with bone growth into a completely porous body. The present invention realizes this advantage and others as provided herein.

SUMMARY OF THE INVENTION

The present invention is directed toward a dental implant for integrating with surrounding bone. The implant includes two separate and distinct bodies, a coronal body and a bone fixation body. Together, these bodies form a complete dental implant.

The coronal body is located at the coronal end of the implant and includes a dental interface adapted to connect with another dental component, such as an abutment. In the preferred embodiment, this interface includes a hexagonal connector, such as a hexagonal protrusion or recess. A threaded bore may be provided to receive a dental screw. The screw assists in connecting the dental component to the dental implant.

Preferably, the coronal body is formed of a solid metal piece, such as titanium or titanium alloy. The body is formed from a machining process and has a generally short, cylindrical shape with a top surface having the dental interface. A smooth, outer transgingival section is provided along the side of the body. This transgingival section protrudes through the gum tissue or gingival tissue in the jawbone of the patient.

The bone fixation body is formed of a porous metal, such as titanium. Preferably, the body is formed with a sintering process, is completely porous, and does not include a metal substrate. In cross section then, the body has a porous structure with no solid metal substrate.

The coronal body (formed of solid metal) and the bone fixation body (formed of a completely porous structure) are permanently connected together. When connected, the two bodies form a dental implant. Preferably, these two bodies are connected with a sintering process.

One important advantage of the present invention is that the body of the implant is completely porous. This porous structure extends entirely through the body of the implant along the region where the implant engages bone. As such, the depth of bone growth into the implant is not restricted to a thin porous coating. Instead, bone can grow completely into and even through the body of the implant. The implant, then, can become fully integrated into surrounding bone with the structure of bone dispersed throughout the body of the implant.

As another advantage, the geometric structure of the porous body is shaped and sized to emulate the shape and size of natural bone surrounding the implant. Specifically, the porous structure of the bone fixation body thus replicates the porous structure of natural bone itself. The porous structure, thus, readily accepts and encourages surrounding bone to grow into and even through the body of the implant.

As another advantage, the bone fixation body may be doped with bone growth agents to enhance and stimulate bone growth. These agents can be placed throughout the bone fixation body so bone grows completely through the implant. Bone growth, as such, is not restricted to the surface of the implant.

As noted, the porous structure of the implant enables bone to grow into and completely through the implant itself. Growth deep into the body of the implant provides an extremely strong interface between the implant and surrounding natural bone. As such, the likelihood that the implant will loosen is greatly reduced. Further, the overall long-term acceptance of the implant in the bone is increased.

Other advantages of the present invention are discussed in connection with the accompanying figures.

DETAILED DESCRIPTION

Figure 1:
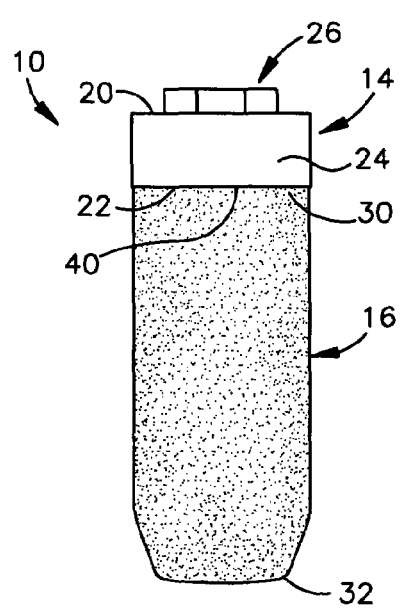
FIG. 1 is a side view of one embodiment of a dental implant of the present invention.
Figure 2:
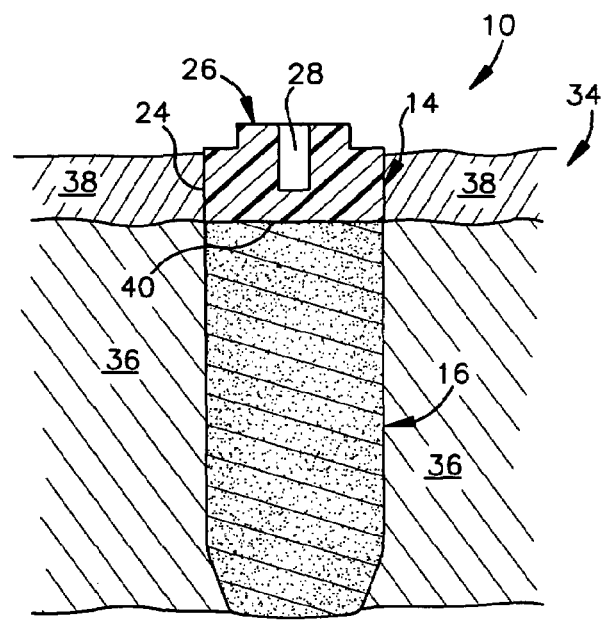
FIG. 2 is a cross-sectional view of the implant of FIG. 1 embedded in a jawbone of a patient.

Referring to FIGS. 1 and 2, an implant 10 is shown according to the invention. Implant 10 is preferably constructed of a biocompatible material such as titanium and includes two primary components or bodies, a coronal body 14 and a bone fixation body 16.

The coronal body 14 has a short cylindrical configuration that extends from a proximal end surface 20 to a distal end surface 22. A transgingival section 24 is formed with a smooth outer surface. A dental interface 26 extends upwardly and adjacent the transgingival section. This interface (also referred to as an abutment-engaging end) is formed as a male hexagonal connector. The interface can have other embodiments known in the art, such as splines, internal and external octagons, stars, and other polygons. A threaded bore 28 extends into the coronal body and is adapted to receive a fixation screw for connecting the dental implant to a dental component, such as an abutment, prosthesis, healing collar, or the like. Preferably, the coronal body 14 is formed of a biocompatible metal, such as a solid metal piece of titanium or titanium alloy. The body can be machined to have a size and shape shown in the figures.

The bone fixation body 16 has an elongated cylindrical shape that extends from a proximal end 30 to a rounded distal end 32. Body 16 is formed from as a porous metal, such as titanium. Preferably, the body has a completely porous structure that extends throughout the entire body from the proximal to distal ends. Specifically, as shown in FIG. 2, body 16 does not include a metal substrate. The distal end surface 22 of coronal body 14 connects or fuses to the proximal end 30 of the bone fixation body 16 at a junction 40.

FIG. 2 shows the implant 10 embedded in a jawbone 34 of a patient. Preferably, the length of the body 16 extends along the region where the implant contacts surrounding bone 36 once the implant is implanted into the jawbone. The transgingival section 24 extends along the gum tissue or gingival tissue 38.

As noted, the bone fixation body 16 has a porous structure that extends from the outer surface and throughout the body. By "porous," it is meant that the material at and under the surface is permeated with interconnected interstitial pores that communicate with the surface. The porous structure can be formed by sintering titanium or titanium alloy powder, metal beads, metal wire mesh, or other suitable materials known in the art.

One advantage of the present invention is that the porous structure of body 16 is adapted for the ingrowth of cancellous and cortical bone spicules. More particularly the size and shape of the porous structure emulates the size and shape of the porous structure of natural bone. Preferably, the average pore diameter of body 16 is about 40 µm to about 800 µm with a porosity from about 45% to 65%. Further, the interconnections between pores can have a diameter larger than 50-60 microns. In short, the geometric configuration of the porous structure should encourage natural bone to migrate and grow into and throughout the entire body 16.

Preferably, body 16 is created with a sintering process. One skilled in the art will appreciate that many variations exist for sintering, and some of these variations may be used to fabricate the present invention. In the preferred embodiment, the coronal body is prepared using conventional and known machining techniques. Next, a ceramic mold is provided. The mold has a first cavity that is sized and shaped to match the size and shape of the bone fixation body. In this first cavity, the sintering material can be placed. The mold also has a second cavity that is adjacent and connected to the first cavity. This second cavity is sized and shaped to receive the coronal body. The coronal body is positioned in the second cavity such that the distal end surface is adjacent and continuous with the first cavity.

The sintering material is then placed into the first cavity. This material may be a titanium alloy powder, such as Ti-6Al-4V. Some of this powder will contact the distal end surface of the coronal body. The mold is then heated to perform the sintering process. During this process, as the material in the first cavity heats and sinters, the bone fixation body forms and simultaneously bonds or fuses to the distal end surface of the coronal body.

The size and shape of the pores and porous structure produced in the first cavity depend on many factors, These factors include, for example, the temperature obtained in the furnace, the sintering time, the size and shape of sintering material, the composition of the sintering material, and the type of ceramic mold used. These factors (and others) can be varied to produce a bone fixation body in accordance with the present invention. Further, these factors (and others) can be varied to produce a strong bond between the bone fixation body and coronal body.

Once the sintering process is finished, the distal surface of the coronal body is directly fused to the bone fixation body. These two bodies are now permanently connected together to form the dental implant.

In the aforementioned sintering process, the bone fixation body simultaneously forms and attaches to the coronal body. One skilled in the art though will appreciate that each of these bodies can be fabricated independently and subsequently connected together. If the bodies are made separately, then they may be attached or fused together using known welding or brazing techniques, for example.

Figure 3:
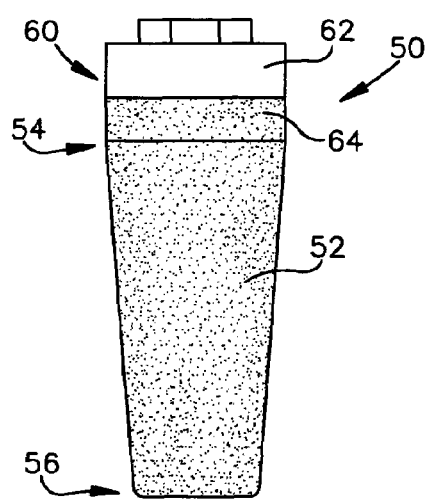
FIG. 3 is a side view of another embodiment of a dental implant of the present invention.
Figure 4:
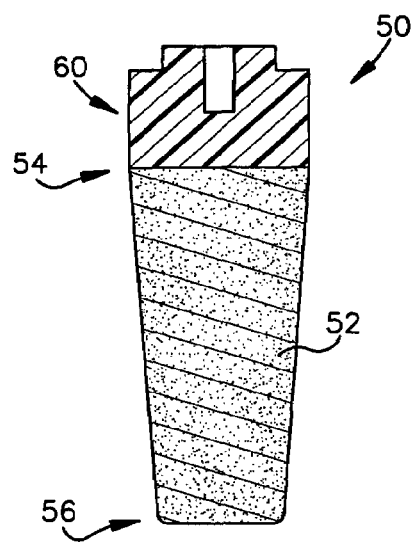
FIG. 4 is a cross-sectional view of FIG. 3.

FIGS. 3 and 4 show another implant 50 according to the invention. With some differences, implant 50 is similarly configured to the implant 10. As one difference, the bone fixation body 52 has a gradual and continuous taper that extends from the proximal end 54 to the distal end 56. Further, the coronal body 60 has two different and distinct regions on the outer surface. A first region 62 has a smooth outer surface. A second region 64 has a bone-engaging surface that is contiguous and adjacent to the first region 62 on one side and contiguous and adjacent the porous bone fixation body 52 on the other side. The second region is non-porous and can be formed with various techniques known in the art. These techniques include, for example, coating with HA, grit-blasting, etching, micro-texturing, other non-porous surface treatments, or combinations of these techniques. This surface is provided as an intermediate zone between the porous body and the smooth first region 62.

Figure 5:
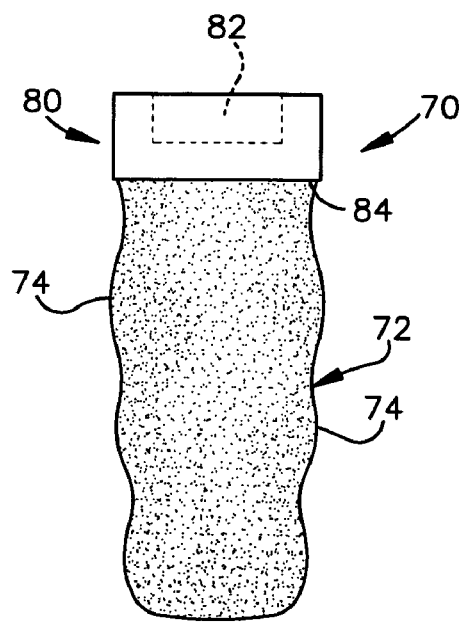
FIG. 5 is a side view of yet another embodiment of a dental implant of the present invention.
Figure 6:
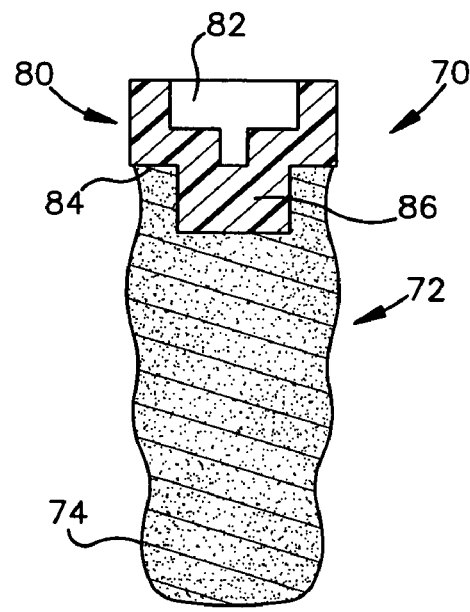
FIG. 6 is a cross-sectional view of FIG. 5.

FIGS. 5 and 6 show another implant 70 according to the invention. With some differences, implant 70 is similarly configured to the implant 10. As one difference, implant 70 has a bone fixation body 72 with an outer surface that has a plurality of undulation 74, such as hills and valleys. These undulations are adapted to firmly secure the implant into the jawbone after the implant is placed therein. Further, the coronal body 80 has a dental interface 82 formed as an internal connection, such as an internal hexagon or other internal polygon. Further yet, the distal end surface 84 of the coronal body has an elongated protrusion 86 extending outwardly. This protrusion extends into the bone fixation body 72 and is adapted to increase the interface between the coronal body and bone fixation body. This protrusion may have various configurations, such as non-tapering, tapering, cylindrical, square, rectangular, hexagonal, octagonal, polygonal, or other shapes. Preferably, the protrusion is formed as a cylinder or square.

Figure 7:
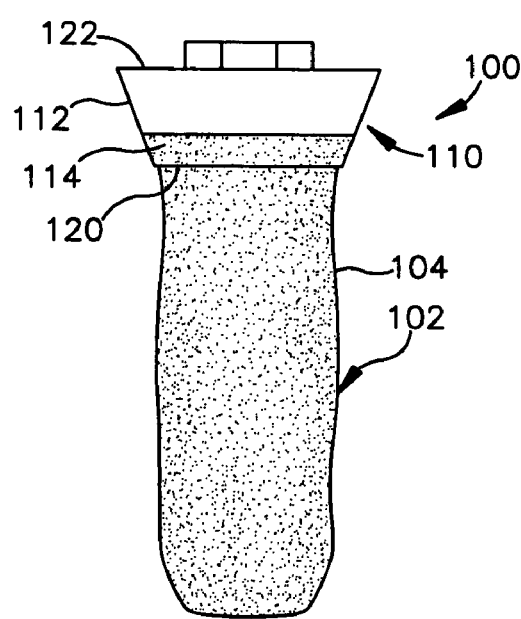
FIG. 7 is side view of another embodiment of a dental implant of the present invention.
Figure 8:
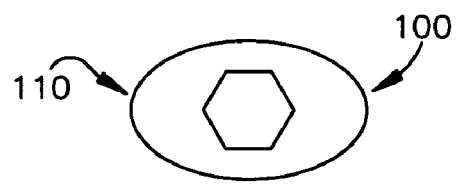
FIG. 8 is a top view of the FIG. 7.

FIGS. 7 and 8 show another implant 100 according to the invention. With some differences, implant 100 is similarly configured to the implant 10. As one difference, implant 100 has a bone fixation body 102 with an uneven outer surface 104. This surface is adapted to aid in bone integration and anti-rotation between the bone fixation body and surrounding bone. Further, the coronal body 110 has two different and distinct regions on the outer surface. A first region 112 has a smooth outer surface; and a second region 114 has a bone-engaging surface. These regions are similar to the regions 62 and 64 described in connection with FIGS. 3 and 4.

As yet another difference, the coronal body 110 has a shape and size adapted to conform to the size and shape of natural teeth. The shape of this body is particularly advantageous in single-stage dental implants. The shape and size of the coronal body can thus contour the gingival or gum tissue to a natural shape that surrounds teeth. The size and shape, for example, can be similar to a molar, premolar, or incisor. FIG. 8 shows a top view of the coronal body 110 to have a shape of an oval or ellipse. As shown in FIG. 7, coronal body can taper upwardly from the distal end 120 to proximal end 122.

Figure 9:
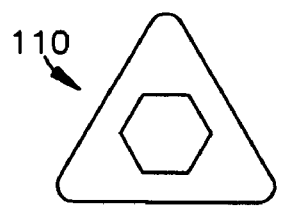
FIG. 9 is an alternate top view of FIG. 7.

FIG. 9 shows a top view of the coronal body 110 in an alternate embodiment to have a triangular shape.

As another advantage of the present invention, the bone fixation body can be adapted to induce bone growth into and entirely through the body. The body, for example, can be doped with biologically active substances. These substances may contain pharmaceutical agents to stimulate bone growth all at once or in a timed-release manner. Such biological active substances are known in the art.

Although illustrative embodiments have been shown and described, a wide range of modifications, changes, and substitutions is contemplated in the foregoing disclosure; and some features of the embodiments may be employed without a corresponding use of other features. Accordingly, it is appropriate that the appended claims be construed broadly and in a manner consistent with the scope of the embodiments disclosed herein.

What is claimed is:

1. A dental implant, comprising:

a coronal body extending from a proximal end to a distal end and formed of a biocompatible metal having a transgingival section and an interface at the proximal end that is adapted to connect to a dental component: and a bone fixation body extending from a proximal end to a distal end and formed of a completely uniform porous structure from the proximal to distal ends, the proximal end of the bone fixation body connected to the distal end of the coronal body, wherein the entire bone fixation body is porous and is adapted to integrate with a jawbone of a patient, wherein the coronal body is non-porous and adapted to extend through gingival tissue of the patient, and wherein the coronal body has a triangular shape.

* * * * *